United States Patent [19]

Abbott et al.

[11] 4,320,052
[45] Mar. 16, 1982

[54] DERIVATIVES OF A-30912A NUCLEUS

[75] Inventors: Bernard J. Abbott, Greenwood; David S. Fukuda, Brownsburg, both of Ind.

[73] Assignee: Eli Lilly and Company, Indianapolis, Ind.

[21] Appl. No.: 181,438

[22] Filed: Aug. 25, 1980

Related U.S. Application Data

[63] Continuation-in-part of Ser. No. 103,030, Dec. 13, 1979, abandoned.

[51] Int. Cl.³ .......................................... C07C 103/52
[52] U.S. Cl. .......................................... 260/112.5 R
[58] Field of Search ................................. 260/112.5 R

[56] References Cited

U.S. PATENT DOCUMENTS

| 3,150,059 | 9/1964 | Kleinschmidt et al. | 260/112.5 R |
|---|---|---|---|
| 3,978,210 | 8/1976 | Mizuno et al. | 260/112.5 R |
| 4,024,245 | 5/1977 | Hoehn et al. | 260/112.5 R |
| 4,024,246 | 5/1977 | Higgens et al. | 260/112.5 R |
| 4,050,989 | 9/1977 | Kuwana et al. | 260/112.5 R |
| 4,173,629 | 11/1979 | Dreyfuss et al. | 260/112.5 R |

FOREIGN PATENT DOCUMENTS

| 834289 | 7/1975 | Belgium | 260/112.5 R |
|---|---|---|---|
| 859067 | 2/1977 | Belgium | 260/112.5 R |
| 866095 | 4/1977 | Belgium | 260/112.5 R |
| 851310 | 8/1977 | Belgium | 260/112.5 R |
| 38-405867 | 7/1963 | Japan | 260/112.5 R |
| 568386 | 4/1972 | Switzerland | 260/112.5 R |

OTHER PUBLICATIONS

T. Kato, et al., J. Antibiotics, 29 (12) 1339–1340 (1976).
S. Chihara, et al., Agr. Biol. Chem., 37 (11), 2455–2463 (1973).
Ibid, 37 (12), 2709–2717 (1973).
Ibid, 38 (3), 521–529 (1974).
Ibid, 38 (10), 1767–1777 (1974).
T. Suzuki, et al., J. Biochem., 56 (4), 335–343 (1964).
J. M. Weber, et al., J. Antibiotics, 31 (4), 373–374 (1978).
J. Shoji, et al., J. Antibiotics, 28, 764–769 (1975).
Ibid, 29 (4), 380–389 (1976).
Ibid, (12) 1268–1274 (1976).
Ibid, (12), 1275–1280 (1976).
F. Benz, et al., Helv. Chim. Acta, 57, 2459 (1974).
C. Keller-Juslen, et al., Tetrahedron Letters, 4147–4150, 1976, vol. 46.
R. Traber, et al., Helv. Chim. Acta, 62, 1252 (1979).

*Primary Examiner*—Delbert R. Phillips
*Attorney, Agent, or Firm*—Nancy J. Harrison; Arthur R. Whale

[57] ABSTRACT

Compounds of the formula

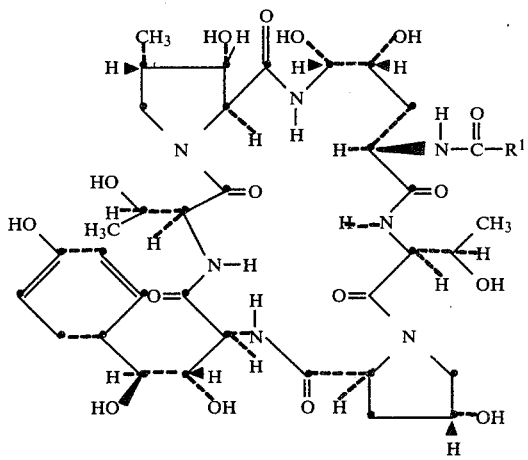

wherein $R^1$ is $C_6$–$C_{24}$ alkyl or $C_6$–$C_{24}$ alkenyl, have antifungal activity.

25 Claims, No Drawings

DERIVATIVES OF A-30912A NUCLEUS

CROSS-REFERENCE TO RELATED APPLICATION

This application is a continuation-in-part of application Ser. No. 103,030, filed Dec. 13, 1979, now abandoned.

BACKGROUND OF THE INVENTION

This invention relates to novel semi-synthetic antifungal compounds which are prepared by the acylation of the cyclic peptide nucleus produced by the enzymatic deacylation of antibiotic A30912 factor A.

Antibiotic A-30912 factor A is an antifungal cyclic peptide having the formula:

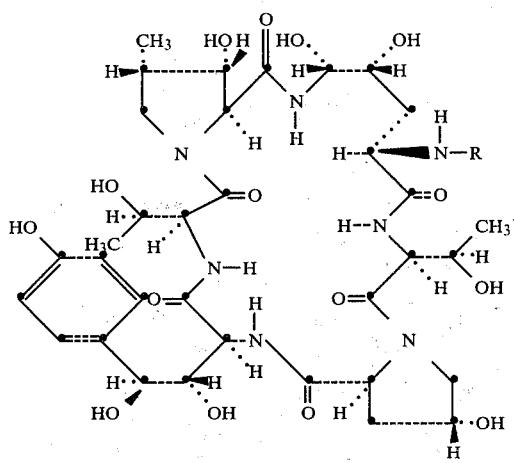

wherein R is the linoleoyl group

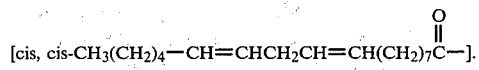

Throughout this application, the cyclic peptide formulas, such as formula I, assume that the amino acids represented are in the L-configuration. The factor is isolated from the A30912 complex which contains other factors arbitrarily designated factors B, C, D, E, F, and G. The A-30912 complex and the individual factors A through G are disclosed by M. Hoehn and K. Michel in U.S. Pat. No. 4,024,245. Antibiotic A-30912 factor A is identical to antibiotic A-22802 which is described by C. Higgins and K. Michel in U.S. Pat. No. 4,024,246. Factor A has also been found to be identical to antibiotic echinocandin B [see F. Benz et al., *Helv. Chim. Acta*, 57, 2459 (1974) and Swiss Pat. No. 568,386] and to antibiotic SL 7810/F [see C. Keller-Juslen et al. *Tetrahedron Letters*, 4147 (1976) and Belgium Pat. No. 834,289, Derwent Abstract 30159X].

Antibiotic A-30912 factor A is prepared by fermentation using one of several different organisms, namely: (a) *Aspergillus rugulosus* NRRL 8113 (see U.S. Pat. No. 4,024,245; (b) *Aspergillus nidulans* NRRL 8112 (see U.S. Pat. No. 4,024,246); (c) *Aspergillus nidulans* var. *echinulatus* A-32204, NRRL 3860, as described in Swiss Pat. No. 568,386; (d) *Aspergillus rugulosus* NRRL 8039 (see Belgian Pat. No. 834,289); or (e) *Aspergillus nidulans* var. *roseus* NRRL 11440 (see copending application of L. Boeck and R. Kastner, METHOD OF PRODUCING THE A-30912 ANTIBIOTICS, Ser. No. 126,078, filed Mar. 3, 1980, which is a continuation-in-part of application Ser. No. 46,744, filed June 8, 1979, (now abandoned), the entire disclosure of which is incorporated herein by reference).

A subculture of *A. nidulans* var. *roseus* has been deposited and made a part of the permanent culture collection of the Northern Regional Research Laboratory, U.S. Department of Agriculture, Agricultural Research Service, Peoria, Ill. 61604, from which it is available to the public under the number NRRL 11440.

When a strain of *A nidulans* var. *roseus* NRRL 11440 is used to produce A-30912 factor A, a complex of factors is obtained which for convenience is called the A-42355 antibiotic complex. A-30912 factor A is the major factor of the A-42355 antibiotic complex, while factors B, D and H are minor factors. Examples 22, 23, and 24 herein, illustrate the preparation of the A-42355 complex and the isolation and purification of A-30912 factor A therefrom. A-30912 factor H is further described in a co-pending application of Karl H. Michel entitled ANTIBIOTIC A-30912 FACTOR H, Ser. No. 117,739, filed Feb. 1, 1980, which is a continuation-in-part of application Ser. No. 46,875, filed June 8, 1979 (now abandoned).

In the antibiotic A-30912 factor A molecule (Formula I), the linoleoyl side chain (R) is attached at the cyclic peptide nucleus at the α-amino group of the dihydroxyornithine residue. Surprisingly, it has been found that the linoleoyl side chain can be cleaved from the nucleus by an enzyme without affecting the chemical intregity of the nucleus. The enzyme employed to effect the deacylation reaction is produced by a microorganism of the family Actinoplanaceae, preferably the microorganism *Actinoplanes utahensis* NRRL 12052, or a variant thereof. To accomplish deacylation, antibiotic A30912 factor A is added to a culture of the microorganism and the culture is allowed to incubate with the substrate until the deacylation is substantially complete. The cyclic nucleus thereby obtained is separated from the fermentation broth by methods known The cyclic nucleus afforded by the aforedescribed enzymatic deacylation of antibiotic A-30912 factor A, is depicted in Formula II.

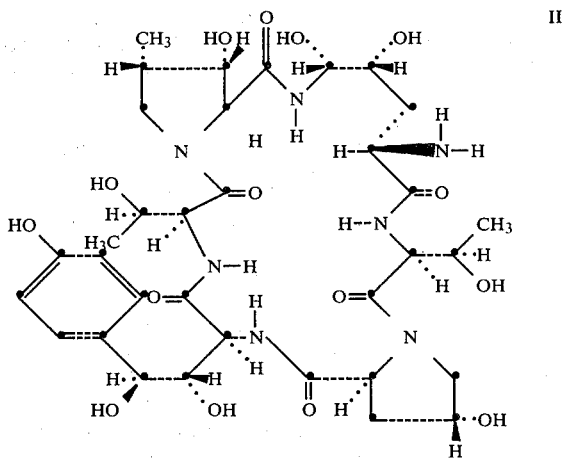

Removal of the side chain group affords a free primary α-amino group in the dihydroxyornithine residue of the cyclic peptide. For convenience, the compound having the structure given in Formula II will be referred to herein as "A-30912A nucleus." As will be apparent to those skilled in the art, A-30912A nucleus can be obtained either in the form of the free amine or of the acid addition salt. Although any suitable acid addition salt may be employed, those which are non-toxic and pharmaceutically acceptable are preferred.

The method of preparing A-30912A nucleus from antibiotic A-30912 factor A by means of fermentation using *Actinoplanes utahensis* NRRL 12052 is described in the co-pending application of Bernard J. Abbott and David S. Fukuda, entitled "A-30912A NUCLEUS", Docket No. X-5229, Ser. No. 103,017, which was filed Dec. 13, 1979. A continuation-in-part application of this application, with the corresponding Ser. No. 181,029, is being filed herewith this even date, the full disclosure of which is incorporated herein by reference. Example 19 herein, illustrates the preparation of A-30912A nucleus by fermentation using antibiotic A-30912 factor A as the substrate and *Actinoplanes utahensis* NRRL 12052 as the microorganism.

The enzyme produced by *Actinoplanes utahensis* NRRL 12052 may be the same enzyme whch has been used to deacylate penicillins (see Walter J. Kleinschmidt, Walter E. Wright, Frederick W. Kavanagh, and William M. Stark, U.S. Pat. No. 3,150,059, issued Sept. 22, 1964).

Cultures of representative species of Actinoplanaceae are available to the public from the Northern Regional Research Laboratory under the following accession numbers:

| | |
|---|---|
| *Actinoplanes utahensis* | NRRL 12052 |
| *Actinoplanes missouriensis* | NRRL 12053 |
| *Actinoplanes* sp. | NRRL 8122 |
| *Actinoplanes* sp. | NRRL 12065 |
| *Streptosporangium roseum* var. *hollandensis* | NRRL 12064 |

The effectiveness of any given strain of microorganism within the family Actinoplanaceae for carrying out the deacylation of this invention is determined by the following procedure. A suitable growth medium is inoculated with the microorganism. The culture is incubated at about 28° C. for two or three days on a rotary shaker. One of the substrate antibiotics is then added to the culture. The pH of the fermentation medium is maintained at about pH 6.5. The culture is monitored for activity using a *Candida albicans* assay. Loss of antibiotic activity is an indication that the microorganism produces the requisite enzyme for deacylation. This must be verified, however, using one of the following methods: (1) analysis by HPLC for presence of the intact nucleus; or (2) re-acylation with an appropriate side chain (e.g. linoleoyl, stearoyl, or palmitoyl) to restore activity.

It is known that other antibiotic substances possess the same nucleus as that of antibiotic A-30912 factor A. These antibiotics differ from antibiotic A-30912 factor A in that different acyl groups are present in place of the linoleoyl group (R) in Formula I. Such antibiotics are: (a) tetrahydro-A-30912 factor A (tetrahydro-SL 7810/F; tetrahydro echinocandin B) described in Belgium Pat. No. 834,289 and by F. Benz et al., *Helv. Chim. Acta*, 57 2459 (1974), which compound is depicted in Formula I when R is stearoyl; and (b) aculaecin A, which is a component of the aculaecin complex (prepared by fermentation using *Aspergillus aculeatus* NRRL 8075) and is described by K. Mizuno et al., in U.S. Pat. No. 3,978,210. As is discussed in Belgium Pat. No. 859,067, in aculaecin A the palmitoyl side chain is present in place of linoleoyl. Tetrahydro-A-30912 factor A can be prepared from antibiotic A-30912 factor A by catalytic hydrogenation using $PtO_2$ in ethanol under positive pressure. Both tetrahydro-A-30912 factor A and aculaecin A can be employed as substrates for the enzymatic deacylation using the procedures herein described.

SUMMARY OF THE INVENTION

The invention sought to be patented comprehends novel compounds derived by acylating A-30912A nucleus (Formula II). The compounds of the present invention have the chemical structure depicted in Formula III:

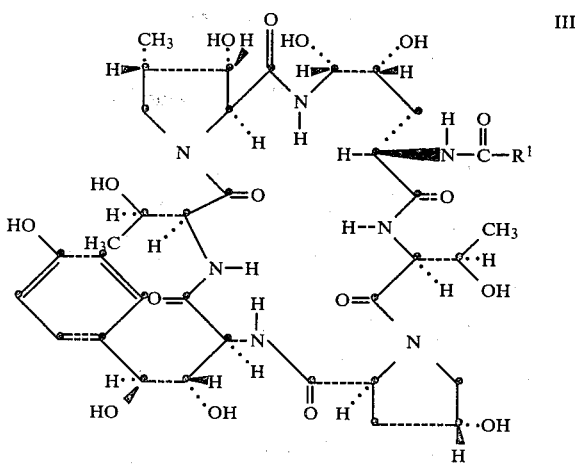

wherein $R^1$ is $C_6$–$C_{24}$ alkyl or $C_6$–$C_{24}$ alkenyl; provided that when $R^1$ is alkyl, $R^1$ cannot be n-tridecyl, n-tetradecyl, n-pentadecyl, or n-heptadecyl; and, when $R^1$ is alkenyl, $R^1$ cannot be cis, cis-$CH_3(CH_2)_4CH=CHCH_2—CH=CH(CH_2)_7—$.

By the term "alkyl" is meant a univalent saturated, straight-chain or branched-chain hydrocarbon radical. By the term "alkenyl" is meant a univalent, unsaturated, straight-chain or branched-chain hydrocarbon radical containing not more than three double bonds. The double bonds of the unsaturated hydrocarbon chain may be either in the cis or trans configuration. By "$C_6$–$C_{24}$" is meant a hydrocarbon (including straight and branched chains) containing from six to 24 carbon atoms.

In subgeneric aspects, the invention contemplates the following preferred embodiments of the compounds of Formula III:

(a) The compounds wherein $R^1$ is alkyl of the formula $CH_3(CH_2)_n—$, wherein n is an integer from 5 to 23, provided that n cannot be 12, 13, 14, or 16.

(b) The compounds wherein $R^1$ is alkyl of the formula $CH_3(CH_2)_n—$, wherein n is 10, 11, 15, 17, 18, 19, or 20.

(c) The compounds wherein $R^1$ is alkyl of the formula

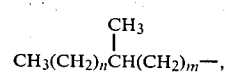

wherein n and m are each, independently, an integer from 0 to 21 provided that n+m must be no less than 3 and no greater than 21.

(d) The compounds wherein $R^1$ is alkenyl containing one cis or trans double bond.

(e) The compounds wherein $R^1$ is cis or trans alkenyl of the formula $$CH_3(CH_2)_nCH=CH(CH_2)_m—$$

wherein n and m are each, independently, an integer from 0 to 21, provided that n+m must be no less than 3 and no greater than 21.

(f) The compounds wherein $R^1$ is alkenyl containing two cis or trans double bonds.

(g) The compounds wherein $R^1$ is cis or trans alkenyl of the formula $$CH_3(CH_2)_nCH=CH(CH_2)_mCH=CH(CH_2)_p—$$

wherein n and p are each, independently, an integer of from 0 to 18 and m is an integer from 1 to 19, provided that m+n+p must be no less than 1 and no greater than 19 and that $R^1$ cannot be linoleoyl.

(h) The compounds wherein $R^1$ is:
cis-$CH_3(CH_2)_5CH=CH(CH_2)_7—$
trans-$CH_3(CH_2)_5CH=CH(CH_2)_7—$
cis-$CH_3(CH_2)_{10}CH=CH(CH_2)_4—$
trans-$CH_3(CH_2)_{10}CH=CH(CH_2)_4—$
cis-$CH_3(CH_2)_7CH=CH(CH_2)_7—$
trans-$CH_3(CH_2)_7CH=CH(CH_2)_7—$
cis-$CH_3(CH_2)_5CH=CH(CH_2)_9—$
trans-$CH_3(CH_2)_5CH=CH(CH_2)_9—$
cis-$CH_3(CH_2)_7CH=CH(CH_2)_9—$
trans-$CH_3(CH_2)_7CH=CH(CH_2)_9—$
cis-$CH_3(CH_2)_7CH=CH(CH_2)_{11}—$
trans-$CH_3(CH_2)_7CH=CH(CH_2)_{11}—$
trans,trans-$CH_3(CH_2)_4CH=CHCH_2CH=CH(CH_2)_7—$
cis,cis,cis-
$CH_3CH_2CH=CHCH_2CH=CHCH_2CH=CH—(CH_2)_7—$

DETAILED DESCRIPTION OF THE INVENTION

The compounds of Formula III inhibit the growth of pathogenic fungi as evidenced by standard biological test procedures. The compounds are useful, therefore, for controlling the growth of fungi on environmental surfaces (as an antiseptic) or in treating infections caused by fungi. The antifungal activity of the compounds has been demonstrated against *Candida albicans* in vitro in agar plate disc diffusion tests and in agar dilution tests, or in vivo in tests in mice infected with *C. albicans*. Thus, the compounds are particularly useful in treating infections caused by strains of *C. albicans* (candidosis). The compounds of Formula III have also shown activity in vitro in agar-plate disc diffusion tests against *Trichophyton mentagrophytes*, a dermatophytic organism. Activity has also been found in in vitro agar plate disc diffusion tests against *Saccharomyces pastorianus*, and *Neurospora crassa*. Certain compounds (as shown in Example 18, Table V) give significant blood levels upon oral administration in mice.

When given to a dog by intravenous administration, 100 mg/kg per day for five days, the compound of Formula III wherein R is n-dodecyl (i.e. the n-tridecanoyl derivative of A-30912 nucleus) showed no outward signs of toxicity, although increased SGPT levels and evidence of hemolysis were observed.

The compounds of Formula III are prepared by acylating A-30912A nucleus at the α-amino group of dihydroxyornithine with the appropriate alkanoyl or alkenoyl side chain using methods conventional in the art for forming an amide bond. The acylation is accomplished, in general, by reacting the nucleus with an activated derivative of the alkanoic acid or alkenoic acid ($R^1CO_2H$) corresponding to the desired acyl side chain group ($R^1CO—$). By the term "activated derivative" is meant a derivative which renders the carboxyl function of the acylating agent reactive to coupling with the primary amino group to form the amide bond which links the acyl side chain to the nucleus. Suitable activated derivatives, their methods of preparation, and their methods of use as acylating agents for a primary amine will be recognized by those skilled in the art. Preferred activated derivatives are: (a) an acid halide (e.g. acid chloride), (b) an acid anhydride (e.g. a alkoxyformic acid anhydride or aryloxyformic acid anhydride) or (c) an activated ester (e.g. a 2,4,5-trichlorophenyl ester). Other methods for activating the carboxyl function include reaction of the carboxylic acid with a carbonyldiimide (e.g. N,N-dicyclohexylcarbodiimide or N,N'-diisopropylcarbodiimide) to give a reactive intermediate which, because of instability, is not isolated, the reaction with the primary amine being carried out in situ.

A preferred method for preparing the compounds of Formula III is by the active ester method. The use of the 2,4,5-trichlorophenyl ester of the desired alkanoic or alkenoic acid as the acylating agent is most preferred. In this method, an excess amount of the active ester is reacted with the nucleus at room temperature in a nonreactive organic solvent such as dimethyl formamide (DMF). The reaction time is not critical, although a time of about 6 to about 20 hours is preferred. At the conclusion of the reaction, the solvent is removed, and the residue is purified such as by reversed phase HPLC using LP-1/C18 as the stationary/phase and a mixture of $H_2O/CH_3OH/CH_3CN$ as the solvent system.

An alternative acylation method is a modified Schotten-Baumann procedure in which the nucleus is treated with the acid chloride of the desired alkanoic acid or alkenoic acid at an alkaline pH. In this method, an excess of the acid chloride in a non-reactive organic solvent (such as acetone) is added slowly to a solution of the nucleus in $[KHPO_4]^-$ buffer (pH 7.5 to 8.0) and acetone. The crude reaction product is separated from the reaction product by extraction into an immiscible organic solvent (chloroform and ethyl acetate). Final purification is by reversed-phase HPLC, as described above.

The alkanoic and alkenoic acids employed as starting materials for the acylation reaction, and the activated derivatives thereof (in particular, the acid chlorides and the 2,4,6-trichlorophenyl esters), are known compounds or can be prepared from known compounds by known methods. The 2,4,5-trichlorophenyl esters are conveniently made by treating the acid chloride of the alkanoic or alkenoic acid with 2,4,5-trichlorophenol in the presence of pyridine or by treating the free alkanoic or alkenoic acid with 2,4,5-trichlorophenol in the presence of N,N'-dicyclohexylcarbodiimide employed as a coupling agent. The 2,4,5-trichlorophenyl ester derivative can be purified by column chromatography over silica gel in toluene.

When employed systemically, the dosage of the compounds of Formula III will vary according to the particular compound being employed, the severity and nature of the infection, and the physical condition of the subject being treated. Therapy should be initiated at low dosages, the dosage being increased until the desired antifungal effect is obtained. The compounds can be administered intravenously or intramuscularly by injection in the form of a sterile aqueous solution or suspension to which may be added, if desired, various conventional pharmaceutically acceptable preserving, buffering, solubilizing, or suspending agents. Other additives, such as saline or glucose may be added to make the solutions isotonic. The proportions and nature of such additives will be apparent to those skilled in the art.

Certain compounds of Formula III give significant blood levels after oral administration (see Example 18) and can be administered systemically by the oral route. For oral use, such compounds can be administered in combination with pharmaceutically acceptable carriers or excipients in the form of capsules, tablets or powders. The nature and proportion of such carriers or excipients will be recognized by those skilled in the art.

When employed to treat vaginal candida infections, the compounds of Formula III can be administered in combination with pharmaceutically acceptable conventional excipients suitable for intravaginal use. Formulations adapted for intravaginal administration will be known to those skilled in the art.

The methods of making and using the compounds of the present invention are illustrated in the following examples:

EXAMPLES 1–16

The preparation of various alkanoyl and alkenoyl derivatives by acylation of A-30912A nucleus, representative of the compounds of Formula III, is shown in Table I, below. The derivatives in Table I are made either by the modified Schotten-Bauman reaction using an acid chloride as acylating agent (method A) or by the active ester method using the 2,4,5-trichlorophenyl ester as the acylating agent (method B). The general procedures for carrying out the acylation reactions by Method A or Method B are set forth below:

Method A (Modified Schotten-Bauman Reaction)

This method involves reaction of A-30912A nucleus with the alkanoic or alkenoic acid chloride which corresponds to the desired acyl side chain.

A-30912A nucleus is dissolved in a mixture of 0.1 M $KHPO_4^-$ buffer, pH 7.5, (5 to 10 ml.) and acetone or methanol (5 to 10 ml.). To the nucleus solution, cooled by an ice-bath or at room temperature, is added slowly (over about a 30-minute period) a solution of the alkanoic or alkenoic acid chloride in acetone (2 to 20 ml). If desired, the pH of the reaction mixture can be adjusted to 7.5 to 8.0 after each addition of the acid chloride; however, this step is not essential. The reaction mixture is stirred at ice bath or at room temperature for 1.5 to 3.0 hour. As the reaction proceeds, a precipitate, which is composed mainly of the free alkanoic or alkenoic acid forms. At the completion of the reaction period, the reaction mixture is centrifuged to remove the precipitate. The collected precipitate and the aqueous supernatant are then treated according to one of the following purification procedures:

Procedure (a) The precipitate is washed one, two, or three times with 2–3 volumes of methanol or methanol-water (1:1). The methanol or methanol-water washes are centrifuged and the methanolic supernatants are combined with the supernatant obtained after the initial centrifugation of the reaction mixture. The combined supernatants are then concentrated in vacuo to remove organic solvent. The aqueous concentrate is then combined with an equal volume of methanol, and the resulting solution is extracted successively with chloroform and ethyl acetate as described above in method (a).

Procedure (b) The precipitate is immediately discarded and the supernatant at pH 5.0–7.0 is extracted one or two times with diethyl ether (equal volume) to remove the unreacted alkanoic or alkenoic acid. The diethyl ether extract is discarded. The extracted supernatant is concentrated in vacuo to remove organic solvent. The aqueous concentrate is then combined with an equal volume of methanol, and the resulting solution is extracted successively with chloroform and ethyl acetate as described above in method (a).

After the extraction step with chloroform followed by ethyl acetate in Procedure (a) or (b) above, all the solvent extract phases are combined and concentrated to dryness to yield the crude alkanoyl or alkenoyl derivative of A-30912A nucleus.

The crude derivative is purified by reversed-phase HPLC as follows: The sample, dissolved in methanol (5–6 ml.), is injected into a ⅝ × 32 in. stainless-steel column packed with LP-1/C18 resin (see Example 25), and the column is eluted with a solvent system comprising $H_2O/CH_3OH/CH_3CN$. The elution is performed at a pressure of 1000–1500 psi with a flow rate of 10–12 ml/hour using an LD-C duplex pump (Milton-Roy). Effluent is monitored with an ISCO-UA-5 detector at 280 nm. The fractions containing the desired product are combined and concentrated to dryness in vacuo to afford and purified alkanoyl or alkenoyl derivative of A-30912A nucleus. The purified product is analyzed by thin layer chromatography (TLC) using reversed-phase $C_{18}$ plates (Whatman $KC_{18}$) and a solvent system comprising 1:2:2 $H_2O/CH_3OH/CH_3CN$. After development, the plates are observed under U.V. light to detect the product. The products are also analyzed by field desorption mass spectrometry (FDMS).

Method B (Active Ester Method)

A solution of A-30912A nucleus and the 2,4,5-trichlorophenyl alkanoate or alkenoate in dimethylformamide (DMF) (10–20 ml.) is stirred at room temperature (RT) for 6–18 hours. The reaction mixture is concentrated in vacuo to dryness to give the crude alkanoyl or alkenoyl derivative of A-30912A nucleus. The crude product is purified by reversed-phase HPLC as described above in Method A. The purified product is analyzed also by the methods employed in Method A.

TABLE I

Alkanoyl and Alkenoyl Derivatives of A-30912A Nucleus

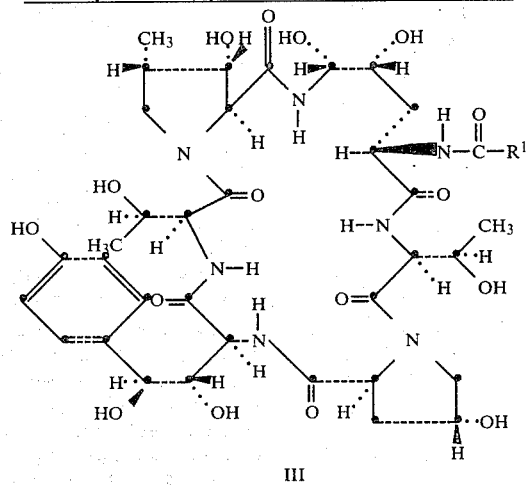

III

| Example No. | R¹ | Acyl. Method | Nucleus wt. (mg.) | Acyl. Agent wt. (mg.) | Reaction Time | HPLC Eluent (v:v:v) $H_2O:CH_3OH:CH_3CN$ | Product wt. (mg.) | $R_f^{(a)}$ | $M^{+(b)}$ |
|---|---|---|---|---|---|---|---|---|---|
| 1. | $CH_3(CH_2)_{10}-$ | B | 150 | 170 | 18 hr | 2:1:2 | 86 | 0.72 | 979 |
| 2. | $CH_3(CH_2)_{11}-$ | B | 150 | 160 | 18 hr | 2:1:2 | 70 | 0.62 | 993 |
| 3. | trans-$CH_3(CH_2)_5-$ $CH=CH(CH_2)_7-$ | B | 340 | 300 | 18 hr | 1:2:2 | 274 | 0.50 | 1033 |
| 4. | cis-$CH_3(CH_2)_5-$ $CH=CH(CH_2)_7-$ | $A^{(c)(g)}$ | 300 | 1000 | 1.5 hr | 1:2:2 | 108 | 0.52 | 1033 |
| 5. | $CH_3(CH_2)_{15}-$ | B | 300 | 260 | 18 hr | 1:4.5:4.5 | 266 | 0.33 | — |
| 6. | cis-$CH_3(CH_2)_{10}-$ $CH=CH(CH_2)_4-$ | B | 300 | 260 | 18 hr | 1:2:2 | 167 | 0.35 | 1084 |
| 7. | cis-$CH_3(CH_2)_7-$ $CH=CH(CH_2)_7-$ | $A^{(d)(g)}$ | 250 | ~1000 | 2 hr | 1:2:2 | 111 | 0.37 | 1061 |
| 8. | trans-$CH_3(CH_2)_7-$ $CH=CH(CH_2)_7-$ | B | 300 | 273 | 16 hr | 1:2:2 | 251 | 0.35 | 1061 |
| 9. | cis-$CH_3(CH_2)_5-$ $CH=CH(CH_2)_9-$ | B | 300 | 273 | 6 hr | 1:2:2 | 262 | 0.38 | 1061 |
| 10. | trans,trans-$CH_3-$ $(CH_2)_4CH=CHCH_2-$ $CH=CH(CH_2)_7-$ | B | 300 | 225 | 16 hr | 1:2:2 | 212 | 0.41 | 1059 |
| 11. | cis,cis,cis-$CH_3-$ $CH_2CH=CHCH_2CH=CH-$ $CH_2CH=CH(CH_2)_7-$ | $A^{(c)(f)}$ | 210 | 1000 | 1.5 hr | 1:2:2 | 150 | .75 | $1058^{(h)}$ |
| 12. | $CH_3(CH_2)_{17}-$ | B | 300 | 285 | 16 hr | 1:4.5:4.5 | 243 | 0.17 | 1077 |
| 13. | $CH_3(CH_2)_{18}-$ | $A^{(e)(f)}$ | 300 | ~1000 | 1.5 hr | 1:4:6 | 84 | 0.13 | 1091 |
| 14. | cis-$CH_3(CH_2)_7-$ $CH=CH(CH_2)_9-$ | B | 300 | 294 | 16 hr | 1:4.5:4.5 | 261 | 0.22 | 1089 |
| 15. | $CH_3(CH_2)_{20}-$ | $A^{(d)(f)}$ | 300 | ~1000 | 1.5 hr | 1:4:6 | 55 | 0.00 | 1119 |
| 16. | cis-$CH_3(CH_2)-$ $CH=CH(CH_2)_{11}-$ | B | 228 | 300 | 16 hr | 1:2:7 | 228 | 0.12 | 117 |

$^{(a)}R_f$ by reversed phase TLC on Whatman $KC_{18}$ plates, flourescent indicator, solvent system 1:2:2 $H_2O:CH_3OH:CH_3CH$
$^{(b)}M^+$ obtained by FDMS. Compound picks up $Na^+$ which is determined with parent mass ion. Results are for $M^+ + Na^+$.
$^{(c)}$At 4–10° C.; in buffer/acetone.
$^{(d)}$At ambient temperature; in buffer/acetone
$^{(e)}$At ambient temperature; in buffer/methanol.
$^{(f)}$Purification method a.
$^{(g)}$Purification method b.
$^{(h)}$Off by one mass unit.

EXAMPLE 17 n-Tridecanoyl Derivative of A-30912A Nucleus

The following procedure illustrates the larger-scale preparation of the compounds of Formula III by the "active ester" method. The specific compound prepared by the procedure given below is the compound of Formula III wherein $R^1$ is $CH_3(CH_2)_{11}-$.

A. Preparation of 2,4,5-trichlorophenyl n-tridecanoate.

A solution of n-tridecanoic acid (Sigma Chemical Co.) (12.5 g.), 2,4,5-trichlorophenol (11.5 g.), and N,N-dicyclohexylcarbodiimide (12.0 g.) in methylene chloride (650 ml.) is stirred at room temperature for 16 hours. The reaction mixture is then filtered and dried in vacuo to give 2,4,5-trichlorophenyl n-tridecanoate (22 g.). The material is purified by column chromatography over silica gel (Woelm) using toluene as the eluent. Fractions are monitored by TLC using a shortwave U.V. light for detection. Fractions containing the purified product are pooled and concentrated in vacuo to dryness.

B. Acylation of A-30912A Nucleus with 2,4,5-trichlorophenyl n-tridecanoate.

A solution of 2,4,5-trichlorophenyl n-tridecanoate (6.0 g.) and A-30912A nucleus (4.5 g.) in dimethylformamide (DMF) (600 ml.) is stirred at room temperature for 16 hours. Removal of solvent in vacuo affords a residue (12 g.). The residue is slurried with methylene chloride (500 ml.) for 45 minutes, and the mixture is filtered. The filtrate is discarded. The remaining solids are extracted with methanol (500 ml.) and the methanol extract is filtered and concentrated in vacuo to give a crude product (5.0 g.).

The crude product is purified by reversed-phase HPLC as follows:

A sample of the crude product (1 g.), dissolved in methanol (5 ml.), is injected into a 1×32 in. stainless steel column packed with LP-1/$C_{18}$ resin (see Example 25). The column is eluted with a solvent system comprising 3:3:4 $H_2O/CH_3OH/CH_3CN$. The elution is performed at a pressure of 1000-1500 psi with a flow rate of 11-12 ml./min using a LDC duplex pump (Milton-Roy). The effluent is monitered by an ultraviolet detector (ISCO-UA-5) at 280 nm. Fractions are collected every two minutes (21-24 ml.). The fractions containing the desired product are pooled and dried in vacuo. Yield of the product: 550 mg. The above-described chromatography is repeated four times with 1-g. samples of crude product to give additional purified samples as follows: 620 mg., 520 mg.; 670 mg., and 490 mg. Total weight of purified title product: 2.8 g. Following the above procedures, 4.0 g. of A-30912A nucleus is reacted with 2,4,5-trichlorophenyl n-tridecanoate to give 2.6 g. of purified title product. The materials from both preparations (5.4 g.) are combined. Mass ion by FDMS: $M^+ + Na^+$:1016. (Theoretical:$M^+ + Na^+$=1016). Analytical HPLC ($C_{18}$ Micro Bondapak, Waters Co.) with eluent system 2:1:2 $H_2O/CH_3OH/CH_3CN$ shows only one peak.

EXAMPLE 18

The antifungal activity of the compounds of Formula III can be demonstrated and elicited in vitro in standard disc-diffusion and agar-dillution tests, or in vivo in standard tests in mice which assess effectiveness against a systemic fungal infection. The results of the antifungal testing of representative compounds of Formula III (Example 1-16) are set forth in Tables II, III, IV, and V.

Tables II and III give the results of the testing in vitro of the compounds of Examples 1-16 by agar-plate disc-diffusion methods. In Table II activity is measured by the size (diameter in mm.) of the observed zone of inhibition of the microorganism produced by the test compound. In Table III, activity is measured by the minimal inhibitory concentration (MIC) of the substance (μg/dic) required to inhibit growth of the test organism. Table IV gives the results of the testing in vitro of the n-tridecanoyl derivative of A30912A nucleus (Formula III, R is n-$C_{12}H_{25}$) against five strains of Candida albicans by the agar dilution method. In Table III activity is measured by the minimal inhibitory concentration (MIC) of the substance (μg/ml) required to inhibit the test organism.

The results of in vivo tests to evaluate the effectiveness of the compound of Examples 1-16 against an infection caused by Candida albicans A-26 in mice are given in Table V, where activity is measured by the $ED_{50}$ value (the dose in mg/kg. required to cure 50% of the test animals). Where an $ED_{50}$ value was not obtained, activity is indicated by the lowest dose at which a significant anti-fungal effect is observed. In this test, groups of male albino mice (specific pathogen free), weighing 18 to 20 grams, are infected intravenously with Candida albicans A-26. The animals are X-irradiated 24 hours prior to infection at about 50 roentgens per minute for 8 minutes (400 total dose) to reduce immune responses to the infecting organism. At 0, 4, and 24 hours post infection each group of mice is given graded doses subcutaneously of the test compound as a suspension in 33% polyethylene glycol-water. The day of death for each animal is recorded. Student's t test statistical comparison of the average day of death is made between each group of infected-treated animals at a particular dosage level and 10 infected-untreated animals to determine if treatment significantly extends survival time.

Table VI gives the results of the testing of the compounds of Example 1-16 for absorption after oral administration. In this test, mice are gavaged with a dose of 416 mg/kg of the test compound suspended in 33% PEG 400-water. At time intervals, blood samples are taken from the orbital sinus and are assyed for antibiotic activity as follows: A 7 mm. disc containing 20 μl of whole blood is placed on agar seeded with Aspergillus montevidensis A35137. After 40 hours incubation at 30° C. zones of inhibition from the blood samples are compared to a standard obtained from the test compound, and the amount of compound in the blood sample is calculated.

TABLE II

Antifungal Activity By The Agar Plate Disc Diffusion Test

| Compound | | Size of zone of inhibition (mm)[a] | | | |
|---|---|---|---|---|---|
| Example No | $R^1$ of Formula III | Saccharomyces pastoranius X-52 | Neurospora crassa 846 | Trichophyton mentagraphytes A-23 | Candida albicans A-26 |
| 1 | $CH_3(CH_2)_{10}-$ | 16 | 40 | [b] | 25 |
| 2 | $CH_3(CH_2)_{11}-$ | 21 | 32* | 60* | 30 |
| 3 | trans-$CH_3(CH_2)_5CH=CH(CH_2)_7-$ | 19 | 40* | 50* | 24 |
| 4 | cis-$CH_3(CH_2)_5CH=CH(CH_2)_7-$ | — | — | — | — |
| 5 | $CH_3(CH)_{15}-$ | 30 | 21 | 40* | 18 |
| 6 | cis-$CH_3(CH_2)_{10}CH=CH(CH_2)_4-$ | 27 | 20 | 34* | 23 |
| 7 | cis-$CH_3(CH_2)_7CH=CH(CH_2)_7-$ | 19 | 18 | 1 | 23 |
| 8 | trans-$CH_3(CH_2)_7CH=CH(CH_2)_7$ | 18 | 32 | 31* | 21 |
| 9 | cis-$CH_3(CH_2)_5CH=CH(CH_2)_9-$ | — | — | — | — |
| 10 | trans,trans-$CH_3(CH_2)_4CH=CHCH_2-CH=CH(CH_2)_7-$ | 24 | 26* | 36 | 24 |
| 11 | cis,cis,cis-$CH_3(CH_2)_2CH=CHCH_2-CH=CHCH_2CH=CH-(CH_2)_7-$ | 16 | 33* | 36 | 30 |
| 12 | $CH_3(CH_2)_{17}-$ | 17 | 18* | 22* | 19 |
| 13 | $CH_3(CH_2)_{18}-$ | 18 | 13 | 16 | 16 |
| 14 | cis-$CH_3(CH_2)_7CH=CH(CH_2)_9-$ | 18 | 18 | 23* | 22 |
| 15 | $CH_3(CH_2)_{20}-$ | 19 | 15 | 20 | 12 |

TABLE II-continued

Antifungal Activity By The Agar Plate Disc Diffusion Test

| Compound | | Size of zone of inhibition (mm)[a] | | | |
|---|---|---|---|---|---|
| Example No | R[1] of Formula III | Saccharomyces pastoranius X-52 | Neurospora crassa 846 | Trichophyton mentagraphytes A-23 | Candida albicans A-26 |
| 16 | cis-$CH_3(CH_2)_7CH=CH(CH_2)_{11}-$ | 12 | 22 | 20* | 12* |

[a] Compounds were tested as suspension in methanol at a concentration of 1 mg/ml. by dipping a 7-mm disc into the suspension and placing it on the agar surface. Incubation: 24-48 hours at 25-37° C.
[b] Too large to read.
*Distinct measurable zone of inhibition with regrowth of organism around disc.

TABLE III

Antifungal Activity By The Agar Plate Disc Diffusion Test

| Compound | | MIC (μg/disc)* | |
|---|---|---|---|
| Example No. | R[1] of Formula III | Candida albicans A-26 | Trichophyton mentagrophytes #6 |
| 1 | $CH_3(CH_2)_{10}-$ | 1.25 | 0.078 |
| 2 | $CH_3(CH_2)_{11}-$ | 0.625 | 0.039 |
| 3 | trans-$CH_3(CH_2)_5CH=CH(CH_2)_7-$ | — | — |
| 4 | cis-$CH_3(CH_2)_5CH=CH(CH_2)_7-$ | 0.312; 0.625 | <0.039 |
| 5 | $CH_3(CH)_{15}-$ | 0.625 | 0.039 |
| 6 | cis-$CH_3(CH_2)_{10}CH=CH(CH_2)_4-$ | 1.25; 1.25 | 0.039 |
| 7 | cis-$CH_3(CH_2)_7CH=CH(CH_2)_7-$ | 0.625; 0.625 | 0.039; 0.156 |
| 8 | trans-$CH_3(CH_2)_7CH=CH(CH_2)_7$ | 0.156 | <0.039 |
| 9 | cis-$CH_3(CH_2)_5CH=CH(CH_2)_9-$ | 0.312 | <0.039 |
| 10 | trans,trans-$CH_3(CH_2)_4CH=CHCH_2CH=CH(CH_2)_7-$ | 0.156 | <0.039 |
| 11 | cis,cis,cis-$CH_3(CH_2)CH=CHCH_2CH=CHCH_2CH=CH-(CH_2)_7-$ | 1.25 | 0.039 |
| 12 | $CH_3(CH_2)_{17}-$ | 2.5; 5.0 | 1.25; 0.625 |
| 13 | $CH_3(CH_2)_{18}-$ | 5.0 | 5 |
| 14 | cis-$CH_3(CH_2)_7CH=CH(CH_2)_9-$ | 1.25; 2.5 | 0.625; 0.156 |
| 15 | $CH_3(CH_2)_{20}-$ | 5.0 | 5 |
| 16 | cis-$CH_3(CH_2)_7CH=CH(CH_2)_{11}-$ | 7.20; 10.0 | 2.5; 2.5 |

*Compounds were suspended in 0.01M sodium borate solution, pH 7.5. The compounds were tested at 20 μg/disc at top level and at two-fold dilutions until end points were reached. Incubation: 24 hours; 30° C.

TABLE IV

In vitro activity of the n-tridecanoyl derivative of A-30912A nucleus against 5 strains of *Candida albicans*.

| MIC (μg/ml) | | | | |
|---|---|---|---|---|
| A26 | SBH 16 | SBH 31 | SBH 28 | SBH 29 |
| 0.312 | 0.625 | 0.625 | 0.625 | 0.625 |

TABLE V

Activity Against *Candida Albicans* A-26 in Mice

| Compound | | | | |
|---|---|---|---|---|
| Example No. | R[1] of Formula III | Dosage* Schedule | ED$_{50}$ (mg/kg)** | Lowest Active Dose (mg/kg) |
| 1 | $CH_3(CH_2)_{10}-$ | B | 62 | 20 |
| 2 | $CH_3(CH_2)_{11}-$ | B | 34 | 20 |
| 3 | trans-$CH_3(CH_2)_5CH=CH(CH_2)_7-$ | A | 40 | 20 |
| 4 | cis-$CH_3(CH_2)_5CH=CH(CH_2)_7-$ | A | >40 | 20 |
| 5 | $CH_3(CH)_{15}-$ | A | 9 | ≧5 |
| 6 | cis-$CH_3(CH_2)_{10}CH=CH(CH_2)_4-$ | A | 18; 20 | 20; 20 |
| 7 | cis-$CH_3(CH_2)_7CH=CH(CH_2)_7-$ | A | 32; 14; 22 | 10; 10; 20 |
| 8 | trans-$CH_3(CH_2)_7CH=CH(CH_2)_7$ | A | 11 | 10 |
| 9 | cis-$CH_3(CH_2)_5CH=CH(CH_2)_9-$ | A | >40 | 40 |
| 10 | trans,trans-$CH_3(CH_2)_4CH=CHCH_2CH=CH(CH_2)_7-$ | A | 16 | 10 |
| 11 | cis,cis,cis-$CH_3(CH_2)CH=CHCH_2CH=CHCH_2CH=CH-(CH_2)_7-$ | A | >40 | >40 |
| 12 | $CH_3(CH_2)_{17}-$ | A | 12; 4.6 | ≧5; ≧5 |
| 13 | $CH_3(CH_2)_{18}-$ | A | 40 | 10 |
| 14 | cis-$CH_3(CH_2)_7CH=CH(CH_2)_9-$ | A | >40; 12.2 | 10; ≧5 |
| 15 | $CH_3(CH_2)_{20}-$ | A | >40 | >40 |
| 16 | cis-$CH_3(CH_2)_7CH=CH(CH_2)_{11}-$ | A | >40; 18 | 40; 10.0 |

*Dosage Schedules: A. = 40, 20, 15, and 10 mg/kg; B = 80, 40, 20, 10 mg/kg. Dosages given 0, 4, and 24 hours post injection as suspension of test compound in 30% PEG—H$_2$O. Number of mice receiving test compounds at each dosage level; 6 mice per group. Number of mice in control (untreated) group: 10 mice per group.
**As measured by increase in survival time of treated animals versus control, calculated by method of Reed v Mueuch, American J. Hygiene, 27, 493 (1938).

TABLE VI
Blood Levels After Oral Administration In Mice

| Example No. | Compound R of Formula III | Blood Levels* (μg/ml) |
|---|---|---|
| 1 | $CH_3(CH_2)_{10}-$ | 0 |
| 2 | $CH_3(CH_2)_{11}-$ | 0.10 |
| 3 | trans-$CH_3(CH_2)_5CH=CH(CH_2)_7-$ | N.T. |
| 4 | cis-$CH_3(CH_2)_5CH=CH(CH_2)_7-$ | 0.19 |
| 5 | $CH_3(CH)_{15}-$ | 97 |
| 6 | cis-$CH_3(CH_2)_{10}CH=CH(CH_2)_4-$ | 18 |
| 7 | cis-$CH_3(CH_2)_7CH=CH(CH_2)_7-$ | 0 |
| 8 | trans-$CH_3(CH_2)_7CH=CH(CH_2)_7$ | 65 |
| 9 | cis-$CH_3(CH_2)_5CH=CH(CH_2)_9-$ | 4.2 |
| 10 | trans,trans-$CH_3(CH_2)_4CH=CHCH_2CH=CH(CH_2)_7-$ | 0.61 |
| 11 | cis,cis,cis-$CH_3(CH_2)CH=CHCH_2CH=CHCH_2CH=CH-(CH_2)_7-$ | 0 |
| 12 | $CH_3(CH_2)_{17}-$ | 54 |
| 13 | $CH_3(CH_2)_{18}-$ | 0 |
| 14 | cis-$CH_3(CH_2)_7CH=CH(CH_2)_9-$ | N.T. |
| 15 | $CH_3(CH_2)_{20}-$ | 0 |
| 16 | cis-$CH_3(CH_2)_7CH=CH(CH_2)_{11}-$ | 0 |

*Four hours after administration of test compound at dose of 416 mg/kg by gavage as suspension of compound in 33% PEG 400-H₂O). Compound determined by bioassay vs. *Aspergillus montevidensis* A-35137.
N.T. - not tested

EXAMPLE 19

Preparation of A-30912A Nucleus

A. Fermentation of *Actinoplanes utahensis* NRRL 12052

A stock culture of *Actinoplanes utahensis* NRRL 12052 is prepared and maintained on an agar slant. The medium used to prepare the slant is selected from one of the following:

MEDIUM A

| Ingredient | Amount |
|---|---|
| Baby oatmeal | 60.0 g |
| Yeast | 2.5 g |
| K₂HPO₄ | 1.0 g |
| Czapek's mineral stock* | 5.0 ml |
| Agar | 25.0 g |
| Deionized water | q.s. to 1 liter |
| pH before autoclaving is about 5.9; adjust to pH 7.2 by addition of NaOH; after autoclaving, pH is about 6.7. | |

*Czapek's mineral stock has the following composition:

| Ingredient | Amount |
|---|---|
| FeSO₄ . 7H₂O (dissolved in 2 ml conc HCl) | 2 g |
| KCl | 100 g |
| MgSO₄ . 7H₂O | 100 g |
| Deionized water | q.s. to 1 liter |

MEDIUM B

| Ingredient | Amount |
|---|---|
| Potato dextrin | 5.0 g |
| Yeast extract | 0.5 g |
| Enzymatic hydrolysate of casein* | 3.0 g |
| Beef extract | 0.5 g |
| Dextrose | 12.5 g |
| Corn starch | 5.0 g |
| Meat peptone | 5.0 g |
| Blackstrap molasses | 2.5 g |
| MgSO₄ . 7H₂O | 0.25 g |
| CaCO₃ | 1.0 g |
| Czapek's mineral stock | 2.0 ml |
| Agar | 20.0 g |
| Deionized water | q.s. to 1 liter |

*N-Z-Amine A, Humko Sheffield Chemical, Lyndhurst, N.J.

The slant is inoculated with *Actinoplanes utahensis* NRRL 12052, and the inoculated slant is incubated at 30° C. for about 8 to 10 days. About ½ of the slant growth is used to inoculate 50 ml of a vegetative medium having the following composition:

| Ingredient | Amount |
|---|---|
| Baby oatmeal | 20.0 g |
| Sucrose | 20.0 g |
| Yeast | 2.5 g |
| Distiller's Dried Grain* | 5.0 g |
| K₂HPO₄ | 1.0 g |
| Czapek's mineral stock | 5.0 ml |
| Deionized water | q.s. to 1 liter |
| adjust to pH 7.4 with NaOH; after autoclaving, pH is about 6.8. | |

*National Distillers Products Co., 99 Park Ave., New York, N.Y.

The inoculated vegetative medium is incubated in a 250-ml wide-mouth Erlenmeyer flask at 30° C. for about 72 hours on a shaker rotating through an arc two inches in diameter at 250 RPM.

This incubated vegetative medium may be used directly to inoculate a second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution [see W. A. Dailey and C. E. Higgens, "Preservation and Storage of Microorganisms in the Gas Phase of Liquid Nitrogen", *Cryobiol* 10, 364–367 (1973) for details]. The prepared suspensions are stored in the vapor phase of liquid nitrogen.

A stored suspension (1 ml) thus prepared is used to inoculate 50 ml of a first-stage vegetative medium (having the composition earlier described). The inoculated first-stage vegetative medium is incubated as above-described.

In order to provide a larger volume of inoculum, 10 ml of the incubated first-stage vegetative medium is used to inoculate 400 ml of a second-stage vegetative medium having the same composition as the first-stage vegetative medium. The second-stage medium is incubated in a two-liter wide-mouth Erlenmeyer flask at 30° C. for about 48 hours on a shaker rotating through an arc two inches in diameter at 250 RPM.

Incubated second-stage vegetative medium (800 ml), prepared as above-described, is used to inoculate 100 liters of sterile production medium selected from one of the following:

MEDIUM I

| Ingredient | Amount (g/L) |
|---|---|
| Peanut meal | 10.0 |
| Soluble meat peptone | 5.0 |
| Sucrose | 20.0 |
| $KH_2PO_4$ | 0.5 |
| $K_2HPO_4$ | 1.2 |
| $MgSO_4 \cdot 7H_2O$ | 0.25 |
| Tap water | q.s. to 1 liter |

The pH of the medium is about 6.9 after sterilization by autoclaving at 121° C. for 45 minutes at about 16–18 psi.

MEDIUM II

| Ingredient | Amount (g/L) |
|---|---|
| Sucrose | 30.0 |
| Peptone | 5.0 |
| $K_2HPO_4$ | 1.0 |
| KCl | 0.5 |
| $MgSO_4 \cdot 7H_2O$ | 0.5 |
| $FeSO_4 \cdot 7H_2O$ | 0.002 |
| Deionized water | q.s. to 1 liter |

Adjust to pH 7.0 with HCl; after autoclaving, pH is about 7.0.

MEDIUM III

| Ingredient | Amount (g/L) |
|---|---|
| Glucose | 20.0 |
| $NH_4Cl$ | 3.0 |
| $Na_2SO_4$ | 2.0 |
| $ZnCl_2$ | 0.019 |
| $MgCl_2 \cdot 6H_2O$ | 0.304 |
| $FeCl_3 \cdot 6H_2O$ | 0.062 |
| $MnCl_2 \cdot 4H_2O$ | 0.035 |
| $CuCl_2 \cdot 2H_2O$ | 0.005 |
| $CaCO_3$ | 6.0 |
| $KH_2PO_4$* | 0.67 |
| Tap water | q.s. to 1 liter |

*Sterilized separately and added aseptically
Final pH about 6.6.

The inoculated production medium is allowed to ferment in a 165-liter fermentation tank at a temperature of about 30° C. for about 42 hours. The fermentation medium is stirred with conventional agitators at about 200 RPM and aerated with sterile air to maintain the dissolved oxygen level above 30% of air saturation at atmospheric pressure.

B. Deacylation of Antibiotic A-30912 Factor A

A fermentation of *A. utahensis* is carried out as described in Sect. A, using slant medium A and production medium I and incubating the production medium for about 42 hours. A-30912 factor A (340 g. of crude substrate which contained about 19.7 g. of A-30912 factor A, dissolved in 1.5 L ethanol) is added to the fermentation medium.

Deacylation of A-30912 factor A is monitored by assay against *Candida albicans*. The fermentation is allowed to continue until deacylation is complete as indicated by disappearance of activity vs. *C. albicans*.

C. Isolation of A-30912A Nucleus

Whole fermentation broth (100 liters), obtained as described in Sect. B and containing nucleus from about 20 g of A-30912 factor A, is filtered. The mycelial cake is discarded. The clear filtrate thus obtained (about 93 liters) is passed through a column containing 4.5 liters of HP-20 resin (DIAION High Porous Polymer, HP-Series, Mitsubishi Chemical Industries Limited, Tokyo, Japan) at a rate of 200 ml/ minute. The effluent thus obtained is discarded. The column is then washed with up to eight column volumes of deionized water at pH 6.5–7.5 to remove residual filtered broth. This wash water is discarded. The column is then eluted with a water:methanol (7:3) solution (85 liters) at a rate of 200–300 ml/minute.

Elution is monitored using the following procedure: Two aliquots are taken from each eluted fraction. One of the aliquots is concentrated to a small volume and is treated with an acid chloride such as myristoyl chloride. This product and the other (untreated) aliquot are assayed for activity against *Candida albicans*. If the untreated aliquot does not have activity and the acylated aliquot does have activity, the fraction contains A-30912A nucleus. The eluate containing the A-30912A nucleus is concentrated under vacuum to a small volume and lyophilized to give approximatey 97 grams of crude nucleus.

D. Purification of A-30912A Nucleus by Reversed-Phase Liquid Chromatography

Crude A-30912A nucleus (25 grams), obtained as described in Section C, is dissolved in 300 ml of water-:acetonitrile:acetic acid:pyridine (96:2:1:1). This solution is chromatographed on a 4-liter stainless-steel column (8 cm × 80 cm) filled with Lichroprep RP-18, particle size 25–40 microns (MC/B Manufacturing Chemists, Inc. E/M, Cincinnati, Ohio). The column is part of a Chromatospac Prep 100 unit (Jobin Yvon, 16–18 Rue du Canal 91160 Longjumeau, France). The column is operated at a pressure of 90–100 psi, giving a flow rate of about 60 ml/minute, using the same solvent. Separation is monitored at 280 nm using a UV monitor (ISCO Absorption Monitor Model UA-5, Instrumentation Specialties Co., 4700 Superior Ave., Lincoln, Nebr. 68504) with an optical unit (ISCO Type 6). Fractions having a volume of about 500 ml are collected each minute.

On the basis of absorption at 280 nm, fractions containing A-30912A nucleus are combined, evaporated under vacuum and lyophilized to give 2.6 grams of nucleus. The amount of solvent required to complete this chromatographic separation process varies from 7–8 liters.

E. Characteristics of A30912A nucleus (a) Empirical formula: $C_{34}H_{51}N_7O_{15}$.

(b) Molecular weight: 797.83.

(c) White amorphous solid, soluble in water, dimethylformamide, dimethylsulfoxide, and methanol; insoluble in chloroform, toluene, and diethylether.

(d) Infrared absorption spectrum (KBr disc.)

Shows absorption maxima at: 3340 broad (OH, H-bonded); 2970, 2930, and 2890 (CH stretch, aliphatic $CH_3$, $CH_2$, CH groups) 1660 and 1625 (several carbonyls C=O); 1510–1550; 1430–1450 (CH wag); 1310–1340; 1230–1260; 1080; 835; 650 broad, and 550 broad $cm^{-1}$.

(e) Electrometric titration in 66% aqueous dimethylformamide indicates the presence of a titratable group with a $pK_a$ value of about 7.35 (initial pH 7.32).

(f) HPLC retention time (K'):11.52 min. under following conditions.
Column: 4×300 mm Packing: silica gel/$C_{18}$
Solvent: ammonium acetate:acetonitrile:water (1:2:97)
Flow Rate: 3 ml/min
Pressure: 2500 psi
Detector: variable wavelength UV at 230 nm
Sensitivity: 0–0.4 A.U.F.S.

EXAMPLE 20

A-30912A nucleus is prepared and purified by the method of Example 19 except that tetrahydro-A-30912A is used as the substrate.

EXAMPLE 21

A-30912A nucleus is prepared and purified by the method of Example 19 except that aculeacin A is used as the substrate.

EXAMPLE 22

Preparation of the A-42355 Antibiotic Complex

A. Shake-Flask Fermentation

A culture of *Aspergillus nidulans* var. *roseus* NRRL 11440 is prepared and maintained on an agar slant prepared with medium having the following composition:

| Ingredient | Amount |
| --- | --- |
| Glucose | 5 g |
| Yeast extract | 2 g |
| $CaCO_3$ | 3 g |
| Vegetable juice* | 200 ml |
| Agar** | 20 g |
| Deionized water | q.s. to 1 liter |

(initial pH 6.1)
*V-8 Juice, Campbell Soup Co., Camden, N.J.
**Meer Corp.

The slant is inoculated with *Aspergillus nidulans* var. *roseus* NRRL 11440, and the inoculated slant is incubated at 25° C. for about seven days. The mature slant culture is covered with water and scraped with a sterile loop to loosen the spores. The resulting suspension is further suspended in 10 ml of sterile deionized water.

One ml of the suspended slant growth is used to inoculate 55 ml of vegetative medium in a 250-ml flask. The vegetative medium has the following composition:

| Ingredient | Amount |
| --- | --- |
| Sucrose | 25 g |
| Blackstrap molasses | 36 g |
| Corn-steep liquor | 6 g |
| Malt extract | 10 g |
| $K_2HPO_4$ | 2 g |
| Enzymatic hydrolysate of casein* | 10 g |
| Tap water | 1100 ml |

(initial pH 6.5–6.7)
*N-Z-Case, Humko Sheffield Chemical, Lyndhurst, N.J.

The inoculated vegetative medium is incubated at 25° C. for 48 hours at 250 rpm on a rotary-type shaker. After 24 hours, the medium is homogenized for one minute at low speed in a blender (Waring type) and then returned to incubation for the remaining 24 hours. Alternatively, the inoculated vegetative medium can be incubated for 48 hours and then homogenized for 15 seconds at low speed.

This incubated vegetative medium may be used to inoculate shake-flask fermentation culture medium or to inoculate a second-stage vegetative medium. Alternatively, it can be stored for later use by maintaining the culture in the vapor phase of liquid nitrogen. The culture is prepared for such storage in multiple small vials as follows:

The vegetative cultures are mixed volume/volume with a suspending solution having the following composition:

| Ingredient | Amount |
| --- | --- |
| Glycerol | 20 ml |
| Lactose | 10 g |
| Deionized water | q.s. to 100 ml |

The prepared suspensions are distributed in small sterile screw-cap tubes (4 ml per tube). These tubes are stored in the vapor phase of liquid nitrogen.

A stored suspension thus prepared can be used to inoculate either agar slants or liquid seed media. Slants are incubated at 25° C. in the light for 7 days.

B. Tank Fermentation

In order to provide a larger volume of inoculum, 10 ml of incubated first-stage vegetative culture is used to inoculate 400 ml of a second-stage vegetative growth medium having the same composition as that of the vegetative medium. The second-stage medium is incubated in a two-liter wide-mouth Erlenmeyer flask at 25° C. for 24 hours on a shaker rotating through an arc two inches in diameter at 250 rpm.

Incubated second-stage medium (800 ml), prepared as above described, is used to inoculate 100 liters of sterile production medium selected from one of the following:

| MEDIUM IV | |
| --- | --- |
| Ingredient | Amount |
| $ZnSO_4 . 7H_2O$ | 0.00455 g/L |
| Soluble meat peptone* | 30.5 g/L |
| Soybean meal | 15.5 g/L |
| Tapioca dextrin** | 2.0 g/L |
| Blackstrap molasses | 10.5 g/L |
| Enzymatic hydrolysate of casein*** | 8.5 g/L |
| $Na_2HPO_4$ | 4.5 g/L |
| $MgSO_4 . 7H_2O$ | 5.5 g/L |
| $FeSO_4 . 7H_2O$ | 0.1 g/L |
| Cottonseed oil | 40.0 ml |
| (Antifoam)**** | 1.0 ml |
| Tap water | 1000.0 ml |

(initial pH 6.8–7.0)
*O.M. Peptone, Amber Laboratories, Juneau, Wisc.
**Stadex 11, A. E. Staley Co., Decatur, Ill.
***N-Z-Amine A, Humko Sheffield Chemical, Lyndhurst, N.J.
****P2000, Dow Corning, Midland, Michigan

| MEDIUM V | |
| --- | --- |
| Ingredient | Amount |
| Glucose | 2.5% |
| Starch | 1.0% |
| Soluble meat peptone* | 1.0% |
| Blackstrap molasses | 1.0% |
| $CaCO_3$ | 0.2% |
| $MgSO_4 . 7H_2O$ | 0.05% |
| Enzymatic hydrolysate of casein** | 0.4% |
| (Antifoam)*** | 0.02% |
| Tap water | q.s. to volume |

*O.M. Peptone
**N-Z-Amine A
***Antifoam "A", Dow Corning

The inoculated production medium is allowed to ferment in a 165-liter fermentation tank at a temperature of 25° C. for about 7 days. The fermentation medium is aerated with sterile air, maintaining the dissolved oxygen level above approximately 50 percent of air saturation.

C. Third-Stage Vegetative Medium

Whenever the fermentation is carried out in tanks larger than those used for 100-liter fermentation, it is recommended that a third-stage vegetative culture be used to seed the larger tank. A preferred third-stage vegetative medium has the following composition:

| Ingredient | Amount |
|---|---|
| Sucrose | 25 g |
| Blackstrap molasses | 25 g |
| Corn-steep liquor | 6 g |
| Enzymatic hydrolysate of casein* | 10 g |
| Malt extract | 10 g |
| K$_2$HPO$_4$ | 2 g |
| Tap water | 1000 ml |

(initial pH 6.1)
*N-Z-Case

EXAMPLE 23

Separation of the A-42355 Antibiotic Complex

Whole fermentation broth (4127 liters), obtained by the method described in Example 22 using production medium V, is stirred thoroughly with methanol (4280 liters) for one hour and then is filtered, using a filter aid (Hyflo Super-cel, a diatomaceous earth, Johns-Manville Products Corp.). The pH of the filtrate is adjusted to pH 4.0 by the addition of 5 N HCl. The acidified filtrate is extracted twice with equal volumes of chloroform. The chloroform extracts are combined and concentrated under vacuum to a volume of about 20 liters. This concentrate is added to about 200 liters of diethyl ether to precipitate the A-42355 complex. The precipitate is separated by filtration to give 2775 g of the A-42355 complex as a gray-white powder.

EXAMPLE 24

Isolation of A-30912 Factor A

The co-pending application of Karl H. Michel entitled RECOVERY PROCESS FOR A-30912 ANTIBIOTICS, Ser. No. 103,014, filed Dec. 13, 1979, describes the reversed-phase high performance, low pressure liquid chromatography (HPLPLC) using silica gel/C$_{18}$ adsorbent as a preferred method for the final purification of A-30912 factor A.

A-42355 antibiotic complex (1 g), prepared as described in Example 22, is dissolved in 7 ml of methanol:water:acetonitrile (7:2:1). This solution is filtered and introduced onto a 3.7-cm I.D.×35-cm glass column [Michel-Miller High Performance Low Pressure (HPLPLC) Chromatography Column, Ace Glass Incorporated, Vineland, N.J. 08360] packed with LP-1/C$_{18}$ silica gel reversed-phase resin (10–20 microns), prepared as described in Example 25, through a loop with the aid of a valve system. The column is packed in methanol:water:acetonitrile (7:2:1) by the slurry-packing procedure described in Example 26. An F.M.I. pump with valveless piston design (maximum flow 19.5 ml/minute) is used to move the solvent through the column at a flow rate of 9 ml/minute at ca. 100 psi, collecting fractions every minute. Elution of the antibiotic is monitored at 280 nm by using a UV monitor (ISCO Model UA-5, Instrument Specialist Co., 4700 Superior Ave., Lincoln, Nebr. 68504) with an optical unit (ISCO Type 6).

The individual A-30912 factors can be identified by the use of thin-layer chromatography (TLC). The $R_f$ values of A-30912 factors A-G, using silica gel (Merck, Darmstadt) TLC, a benzene:methanol (7:3) solvent system, and *Candida albicans* bioautography are given in Table VII.

TABLE VII

| A-30912 Factor | $R_f$ Value |
|---|---|
| A | 0.35 |
| B | 0.45 |
| C | 0.54 |
| D | 0.59 |
| E | 0.27 |
| F | 0.18 |
| G | 0.13 |

The approximate $R_f$ values of A-30912 factors A, B, C, D, and H in different solvent systems, using silica gel TLC (Merck-Darmstadt silica gel #60 plates, 20×20 cm) and *Candida albicans* bioautography, are given in Table VIII.

TABLE VIII

| A-30912 Factor | $R_f$ Values - Solvent Systems | | | |
|---|---|---|---|---|
| | a | b | c | d |
| Factor A | 0.28 | 0.14 | 0.28 | 0.43 |
| Factor B | 0.39 | 0.21 | 0.42 | 0.47 |
| Factor C | 0.46 | 0.31 | 0.51 | 0.58 |
| Factor D | 0.50 | 0.38 | 0.57 | 0.61 |
| Factor H | 0.42 | 0.27 | 0.36 | 0.53 |

Solvent Systems
a: ethyl acetate:methanol (3:2)
b: ethyl acetate:methanol (7:3)
c: acetonitrile:water (95:5)
d: ethyl acetate:ethanol:acetic acid (40:60:0.25)

A-30912 factors A, B, D and H can also be identified by analytical HPLPLC using the following conditions:

| | |
|---|---|
| Column: | glass, 0.8 × 15.0 cm |
| Packing: | Nucleosil ® 10-C$_{18}$ (Machery-Nagel and Company); packed using slurry-packing procedure of Example 8 |
| Solvent: | methanol:water:acetonitrile (7:2:1) |
| Sample Volume: | 8 mcl |
| Sample Size: | 8 mcg |
| Column Temperature: | ambient |
| Flow Rate: | 1.8 ml/min |
| Pressure: | ca. 200 psi |
| Detector: | UV at 222 nm (ISCO Model 1800 Variable Wavelength UV-Visible Absorbance Monitor) |
| Pump: | LDC Duplex Minipump |
| Injection: | loop injection |

The approximate retention times for A-30912 factors A, B, D, and H under these conditions are summarized in Table IX.

TABLE IX

| A-30912 Factor | Retention Time (seconds) |
|---|---|
| A | 792 |
| B | 870 |
| H | 990 |

TABLE IX-continued

| A-30912 Factor | Retention Time (seconds) |
| --- | --- |
| D | 1,140 |

EXAMPLE 25

Preparation of Silica Gel/$C_{18}$ Reversed Phase Resin

Step 1: Hydrolysis

LP-1 silica gel (1000 g from Quantum Corp., now Whatman) is added to a mixture of concentrated sulfuric acid (1650 ml) and concentrated nitric acid (1650 ml) in a 5-L round-bottom flask and shaken for proper suspension. The mixture is heated on a steam bath overnight (16 hours) with a water-jacketed condenser attached to the flask.

The mixture is cooled in an ice bath and carefully filtered using a sintered-glass funnel. The silica gel is washed with deionized water until the pH is neutral. The silica gel is then washed with acetone (4 L) and dried under vacuum at 100° C. for 2 days.

Step 2: First Silylation

The dry silica gel from Step 1 is transferred to a round-bottom flask and suspended in toluene (3.5 L). The flask is heated on a steam bath for 2 hours to azeotrope off some residual water. Octadecyltrichlorosilane (321 ml, Aldrich Chemical Company) is added, and the reaction mixture is refluxed overnight (16 hours) with slow mechanical stirring at about 60° C. Care is taken so that the stirrer does not reach near the bottom of the flask. This is to prevent grinding the silica gel particles.

The mixture is allowed to cool. The silanized silica gel is collected, washed with toluene (3 L) and acetone (3 L), and then air-dried overnight (16–20 hours). The dried silica gel is suspended in 3.5 L of acetonitrile:water (1:1) in a 5-L flask, stirred carefully at room temperature for 2 hours, filtered, washed with acetone (3 L) and air-dried overnight.

Step 3: Second Silylation

The procedure from the first silylation is repeated using 200 ml of octadecyltrichlorosilane. The suspension is refluxed at 60° C. for 2 hours while stirring carefully. The final product is recovered by filtration, washed with toluene (3 L) and methanol (6 L), and then dried under vacuum at 50° C. overnight (16–20 hours).

EXAMPLE 26

Slurry Packing Procedure for Michel-Miller Columns

General Information

This procedure is employed for packing silica gel $C_{18}$ reversed phase resin such as that prepared by the method of Example 25. Generally, a pressure of less than 200 psi and flow rates between 5–40 ml/minute are required for this slurry packing technique; this is dependent on column volume and size. Packing pressure should exceed the pressure used during actual separation by 30–50 psi; this will assure no further compression of the adsorbent during separation runs. A sudden decrease in pressure may cause cracks or channels to form in the packing material, which would greatly reduce column efficiency. Therefore, it is important to let the pressure drop slowly to zero whenever the pump is turned off.

The approximate volume of columns (Ace Glass Cat. No., unpacked) are No. 5795-04, 12 ml; No. 5795-10, 110 ml; No. 5795-16, 300 ml; No. 5795-24, 635 ml; and No. 5796-34, 34 ml.

The time required to pack a glass column will vary from minutes to several hours depending on column size and the experience of the scientist.

EXAMPLE

1. Connect glass column to a reservoir column via coupling (volume of reservoir column should be twice that of the column). Place both columns in vertical positions (reservoir column above).

2. Weigh out packing material (ca. 100 g for 200 ml column).

3. Add ca. five volumes of solvent to packing material; use a mixture of 70–80% methanol and 20–30% water.

4. Shake well until all particles are wetted, let stand overnight or longer to assure complete soaking of particles by solvent. Decant supernatant liquid.

5. Slurry the resin with sufficient solvent to fill reservoir column. Pour swiftly into reservoir. The column must be pre-filled with the same solvent and the reservoir column should be partly filled with solvent before slurry is poured. The use of larger slurry volumes may also provide good results; however, this will require (a) larger reservoir or (b) multiple reservoir fillings during the packing procedure.

6. Close reservoir with the Teflon plug beneath the column (see FIG. 1 of U.S. Pat. No. 4,131,547, plug No. 3); connect to pump; and immediately start pumping solvent through system at maximum flow rate if Ace Cat. No. 13265-25 Pump or similar solvent-delivery system is used (ca. 20 ml/minute).

7. Continue until column is completely filled with adsorbent. Pressure should not exceed maximum tolerance of column during this operation (ca. 200 psi for large columns and 300 psi for analytical columns). In most cases, pressures less than 200 psi will be sufficient.

8. Should pressure exceed maximum values, reduce flow-rate; pressure will drop.

9. After column has been filled with adsorbent, turn off pump; let pressure drop to zero; disconnect reservoir; replace reservoir with a pre-column; fill pre-column with solvent and small amount of adsorbent; and pump at maximum pressure until column is completely packed. For additional information, see general procedure. Always allow pressure to decrease slowly after turning off pump—this will prevent formation of any cracks or channels in the packing material.

10. Relieve pressure and disconnect pre-column carefully. With small spatula remove a few mm (2–4) of packing from top of column; place 1 or 2 filter(s) in top of column; gently depress to top of packing material, and place Teflon plug on top of column until seal is confirmed. Connect column to pump, put pressure on (usually less than 200 psi) and observe through glass wall on top of column if resin is packing any further. If packing material should continue to settle (this may be the case with larger columns), some dead space or channelling will appear and step 9 should be repeated.

EXAMPLE 27

Preparation of Tetrahydro-A-30912A

A-30912 factor A is dissolved in ethanol. $PtO_2$ in absolute ethanol is reduced to form Pt, which in turn is used to reduce the A-30912 factor A catalytically, using hydrogenation under positive pressure until the reaction is complete (about 2-3 hours). The reaction mixture is filtered and concentrated under vacuum. The residue is dissolved in a small amount of tert-butanol and lyophilized to give tetrahydro-A-30912A.

What is claimed is:

1. A compound of the formula:

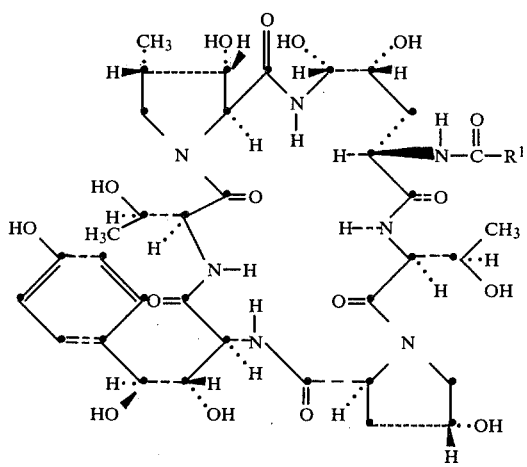

wherein $R^1$ is $C_6$–$C_{24}$ alkyl or $C_6$–$C_{24}$ alkenyl, provided that when $R^1$ is alkyl, $R^1$ cannot be n-tridecyl n-tetradecyl, n-pentadecyl, or n-heptadecyl; and, when $R^1$ is alkenyl, $R^1$ cannot be cis,cis-$CH_3(CH_2)_4CH=CHCH_2-CH=CH(CH_2)_7-$.

2. A compound as defined in claim 1 wherein $R^1$ is $C_6$–$C_{24}$ alkyl.

3. A compound as defined in claim 2 wherein $R^1$ is alkyl of the formula $CH_3(CH_2)_n$ wherein n is an integer from 5 to 23, provided that n cannot be 12, 13, 14, or 16.

4. The compound as defined in claim 3 wherein $R^1$ is $CH_3(CH_2)_{10}-$.

5. The compound as defined in claim 3 wherein $R^1$ is $CH_3(CH_2)_{11}-$.

6. The compound as defined in claim 3 wherein $R^1$ is $CH_3(CH_2)_{15}-$.

7. The compound as defined in claim 3 wherein $R^1$ is $CH_3(CH_2)_{17}-$.

8. The compound as defined in claim 3 wherein $R^1$ is $CH_3(CH_2)_{18}-$.

9. The compound as defined in claim 3 wherein $R^1$ is $CH_3(CH_2)_{19}-$.

10. The compound as defined in claim 3 wherein $R^1$ is $CH_3(CH_2)_{20}-$.

11. A compound as defined in claim 2 wherein $R^1$ is alkyl of the formula $$CH_3(CH_2)_nCH(CH_2)_m- \atop |\ CH_3$$

wherein n and m are each, independently, an integer of from 0 to 21, provided that n+m must be no less than 3 and no greater than 21.

12. A compound as defined in claim 1 wherein $R^1$ is $C_6$–$C_{24}$ alkenyl containing one cis- or trans-double bond.

13. A compound as defined in claim 12 wherein $R^1$ is cis- or trans-alkenyl of the formula $$CH_3(CH_2)_nCH=CH(CH_2)_m-.$$

wherein n and m are each independently an integer from 0 to 21, provided that n+m must be no less than 3 and no greater than 21.

14. The compound as defined in claim 13 wherein $R^1$ is cis-$CH_3(CH_2)_5CH=CH(CH_2)_7-$.

15. The compound as defined in claim 13 wherein $R^1$ is trans-$CH_3(CH_2)_5CH=CH(CH_2)_7-$.

16. The compound as defined in claim 13 wherein $R^1$ is cis-$CH_3(CH_2)_{10}CH=CH(CH_2)_4-$.

17. The compound as defined in claim 13 wherein $R^1$ is cis-$CH_3(CH_2)_7CH=CH(CH_2)_7-$.

18. The compound as defined in claim 13 wherein $R^1$ is trans-$CH_3(CH_2)_7CH=CH(CH_2)_7-$.

19. The compound as defined in claim 13 wherein $R^1$ is cis-$CH_3(CH_2)_5CH=CH(CH_2)_9-$.

20. The compound as defined in claim 13 wherein $R^1$ is cis-$CH_3(CH_2)_7CH=CH(CH_2)_9-$.

21. The compound as defined in claim 13 wherein $R^1$ is cis-$CH_3(CH_2)_7CH=CH(CH_2)_{11}-$.

22. A compound as defined in claim 1 wherein $R^1$ is $C_6$–$C_{24}$ alkenyl containing two cis- or trans-double bond.

23. The compound as defined in claim 22 wherein $R^1$ is trans,trans-$CH_3(CH_2)_4CH=CHCH_2CH=CH(CH_2)_7-$.

24. A compound as defined in claim 1 wherein $R^1$ is $C_6$–$C_{24}$ alkenyl containing three cis- or trans-double bond.

25. The compound as defined in claim 24 wherein $R^1$ is cis,cis,cis-$CH_3CH_2CH=CHCH_2CH=CHCH_2-CH=CH(CH_2)_7-$.

* * * * *